(12) United States Patent
Seth et al.

(10) Patent No.: US 12,740,884 B2
(45) Date of Patent: Sep. 22, 2026

(54) ORTHOPEDIC SYSTEM AND METHOD

(71) Applicant: VispalExo Inc., Wilmington, DE (US)

(72) Inventors: Ajay K. Seth, North Canton, OH (US); Jeffrey A. Denune, Indianapolis, IN (US); Chandan Sen, Indianapolis, IN (US); David M. Uhlenhake, Toledo, OH (US)

(73) Assignee: VispalExo Inc., North Canton, OH (US)

( * ) Notice: Subject to any disclaimer, the term of this patent is extended or adjusted under 35 U.S.C. 154(b) by 135 days.

(21) Appl. No.: 18/411,745

(22) Filed: Jan. 12, 2024

(65) Prior Publication Data

US 2024/0238111 A1 Jul. 18, 2024

Related U.S. Application Data

(60) Provisional application No. 63/479,670, filed on Jan. 12, 2023.

(51) Int. Cl.
*A61F 5/01* (2006.01)

(52) U.S. Cl.
CPC ...... *A61F 5/013* (2013.01); *A61F 2005/0134* (2013.01); *A61F 2005/0146* (2013.01); *A61F 2005/0181* (2013.01)

(58) Field of Classification Search
CPC ........ A61F 5/013; A61F 13/107; A61F 5/373; A61F 5/3738; A61F 5/30; A61F 5/05875; A61F 5/05866; A61F 2005/0172; A61G 13/0045; A61H 1/0277; A61H 1/0285; A61H 1/0288
USPC ...................................................... 602/16, 21
See application file for complete search history.

(56) References Cited

U.S. PATENT DOCUMENTS

| | | | | |
|---|---|---|---|---|
| 5,086,760 A * | 2/1992 | Neumann | A61F 5/0127 606/26 |
| 5,407,420 A * | 4/1995 | Bastyr | A61F 5/013 602/5 |
| 5,472,410 A * | 12/1995 | Hamersly | A61F 5/0125 601/33 |
| 2010/0016766 A1* | 1/2010 | Zhang | A61H 1/0274 601/5 |
| 2010/0160986 A1* | 6/2010 | Simmons | A61H 23/02 607/3 |
| 2018/0280180 A1* | 10/2018 | Amari | A61H 1/0237 |

(Continued)

FOREIGN PATENT DOCUMENTS

| | | | |
|---|---|---|---|
| WO | WO-2020183049 A1 * | 9/2020 | A61H 1/0274 |
| WO | 2022076039 A1 | 4/2022 | |

OTHER PUBLICATIONS

WO-2020183049-A1 translated (Year: 2020).*
Written Opinion of the International Searching Authority dated May 23, 2024.

*Primary Examiner* — Alireza Nia
*Assistant Examiner* — Michael Milo
(74) *Attorney, Agent, or Firm* — Jacob M. Ward; Ward Law Office LLC

(57) ABSTRACT

The present disclosure provides an orthopedic brace for a limb. The orthopedic brace can include an upper portion, a lower portion, and a multi-axial joint. The multi-axial joint can connect the upper portion and the lower portion and can further a stacked joint assembly configured to rotate about multiple axes. A method of operating an orthopedic system is also provided.

17 Claims, 13 Drawing Sheets

(56) References Cited

U.S. PATENT DOCUMENTS

2020/0000619 A1* 1/2020 Schipman ............. A61F 5/0123
2020/0360169 A1 11/2020 Kelly et al.
2021/0228430 A1 7/2021 Farris et al.
2021/0401607 A1* 12/2021 Sanderson .............. A61F 5/013

* cited by examiner

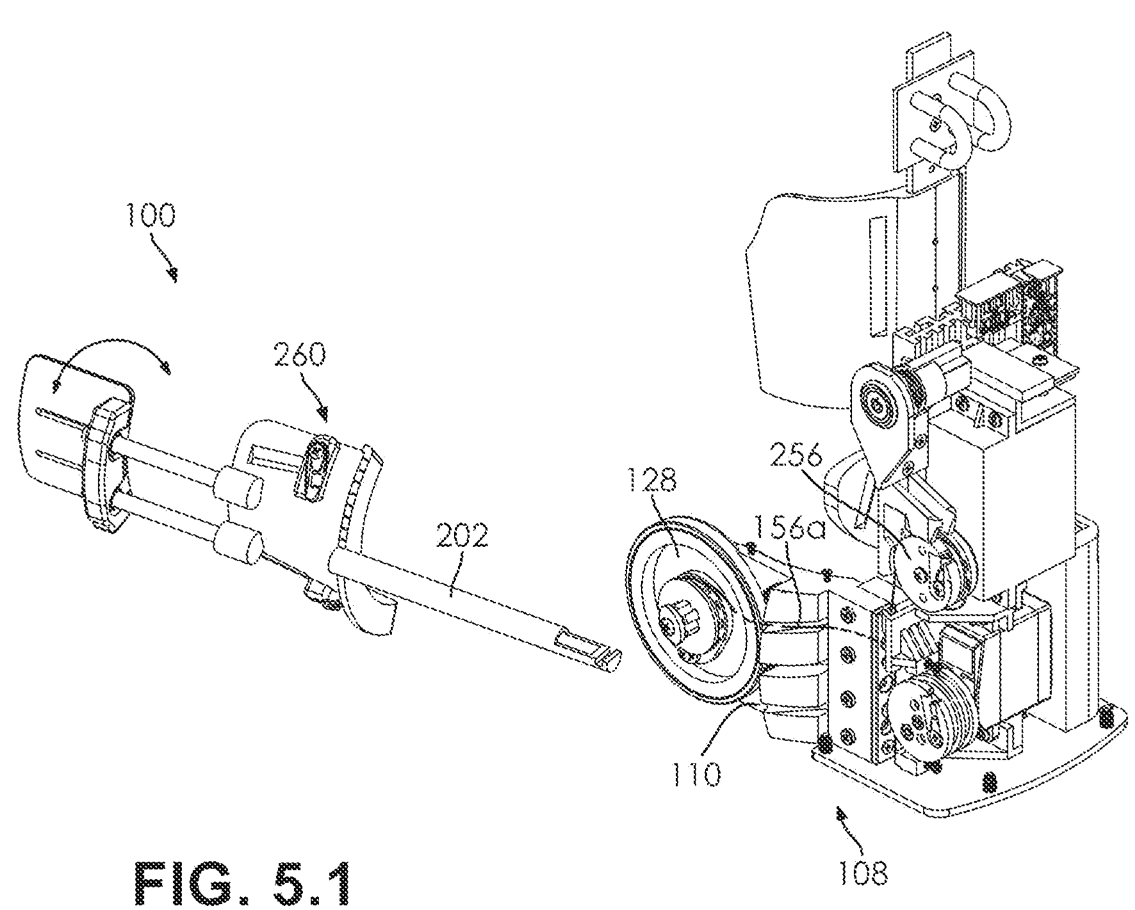
FIG. 5.1

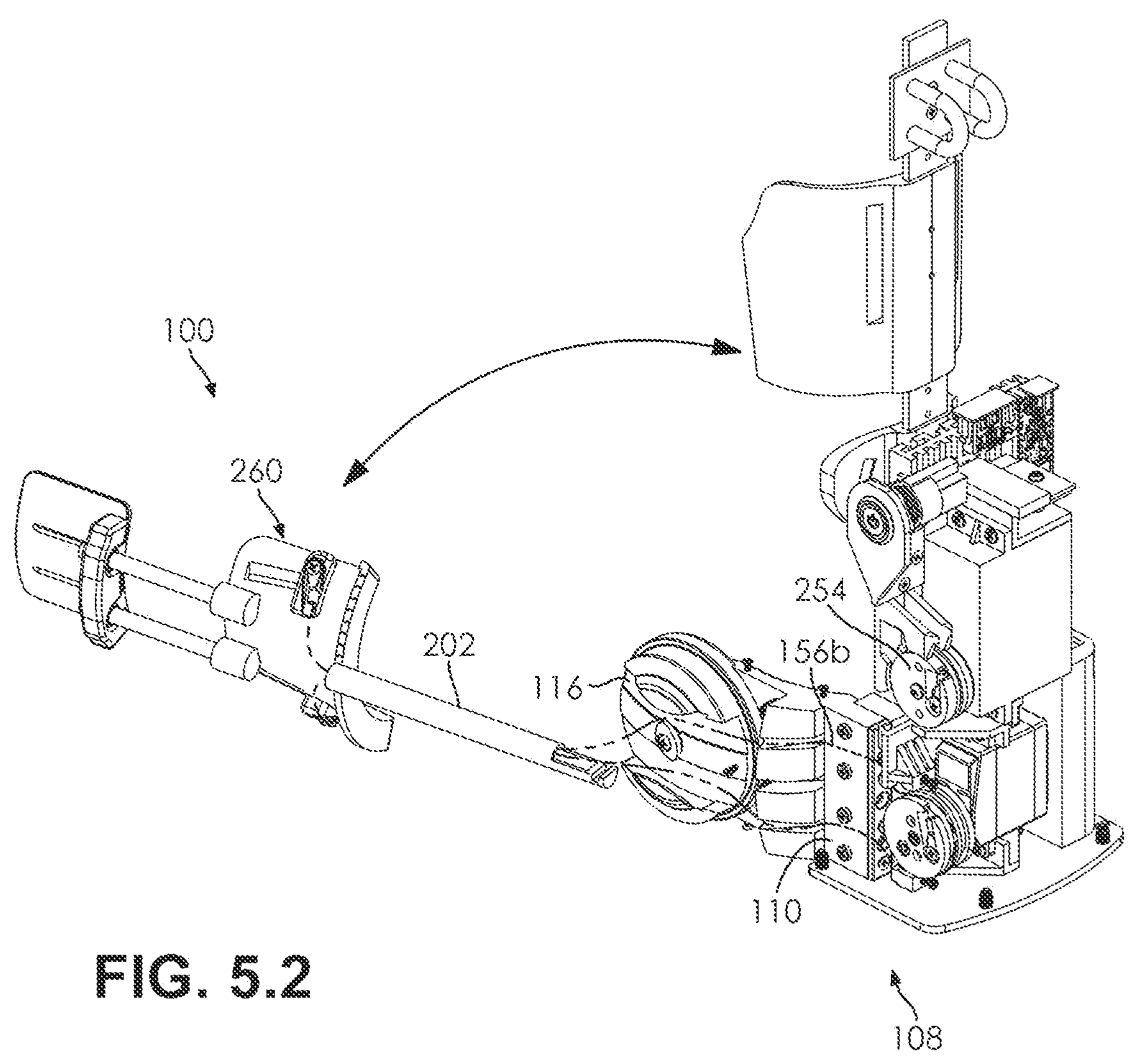
FIG. 5.2

ORTHOPEDIC SYSTEM AND METHOD

CROSS-REFERENCE TO RELATED APPLICATIONS

This application claims the benefit of U.S. Provisional Application No. 63/479,670, filed on Jan. 12, 2023. The entire disclosure of the above application is incorporated herein by reference.

FIELD

The present technology relates to medical orthopedic braces for limb and joint rehabilitation.

INTRODUCTION

This section provides background information related to the present disclosure which is not necessarily prior art.

Orthopedic devices or braces are commonly used by medical professionals to help protect and/or rehabilitate the limb or joint of a patient post injury and/or post surgery. In some situations, such devices are utilized beyond just protecting and/or rehabilitation of a limb because the patient has completely and permanently lost the ability to actively control the function of the anatomical joint due to a traumatic injury or illness. For example, quadriplegic patients completely lose their ability to move a limb around a joint due to an injury that prevents, or significantly reduces, an operable interface between the brain and the muscles coupled to the bone components of the joint. In this situation the affected muscles are incapable of receiving a signal from the patient's brain to execute a desired movement. Rehabilitation is unfortunately not an option in this scenario and it is therefore desirable to have an orthopedic system capable of being operably interfaced with a patient's brain so the patient can instruct the brace to execute a number of operations; e.g., when the patient desires to flex and extend their arm around the elbow joint. The ability to move their arm in this manner significantly enhances the patient's personal independence, and accordingly, their quality of life.

To achieve the enhancement of personal independence, however, an orthopedic system should include the following characteristics: (i) a brace having appropriately coupled components, (ii) an actuator for moving the components of the brace, and (iii) a mechanism that provides an operable interface between the patient's brain and actuator so the patient can effectively communicate with the actuator and execute the instructed movement. Accordingly, an orthopedic system that includes the aforementioned characteristics is desirable, and particularly desirable for patients who have completely lost their ability to move a limb, e.g., a quadriplegic patient. However, current orthopedic systems suffer from a number of draw backs in attempting to enhance a patient's independence in the above-described manner.

There are a number of orthopedic systems that utilize surgically implanted sensors to provide an operable interface between the patient's brain and the actuator. However, these systems come along with costs and inherent risks associated with surgery. Other systems utilize actuators that are activated by signals generated by the muscles that are operatively coupled to the joint of the damaged limb. In such cases, the damaged limb is positioned in the orthopedic brace and sensors are placed to detect signals from muscles surrounded by the brace. These types of arrangements require the muscles within the brace to still be able to voluntarily contract so a signal can be sent to the actuator.

Such arrangements will not work with a patient who has lost an operable interface between the brain and the muscles since these muscles cannot voluntarily contract and generate a signal to activate an actuator. Current orthopedic systems also tend to be bulky, heavy, and complex which increases their cost and limits their ability to be worn under clothes. Furthermore, some of these systems require more than one sensor which further increases complexity and cost.

Braces used in present orthopedic systems also have significant draw backs. For example, these braces present fit and function challenges, where present orthopedic braces are typically designed as a one-size-fits-all brace with a single-axle hinge joint that only allows the patient to move between extended and flexed positions. Such braces often have fit and alignment issues because the limb of the user, such as the arm, is not perfectly straight. For example, the carrying angle for most users can be about 5 degrees or greater than 5 degrees in some cases. Certain braces, such as single-axle braces, further fail to account for the carrying angle of the user's arm, which often causes the axis of the brace to be offset from the axis of the joint. As such, single-axle braces often limit the full range of motion of the user's joint because of the abnormal fit and alignment. The limited full range of motion can then hinder the use of the limb. Additionally, common orthopedic braces do not allow pronation and supination movements of the arm, which further minimizes the joint's range or motion. Common orthopedic braces are also often configured as passive braces that require movement from the user. Such passive braces do not allow the user, such as patients with hemiplegia/paraplegia from a stroke, spinal cord injury, or other injury or illness, a sense of independence since such passive braces require movement from the patient or user.

A motorized orthopedic brace that requires no movement from the patient may be desirable in cases where a patient has a permanent loss of muscle function. These include motorized braces that replicate the natural biological function and anatomical movements of the limb as closely as possible. By using an orthopedic brace that has sensors and mechanisms designed and positioned as to replicate the biological anatomical movements of the limb, the risk of discomfort and shearing is greatly reduced. Shearing may cause skin tears and loosen the brace in use.

Accordingly, there is need for an orthopedic brace for a limb, such as for an arm, that better replicates the correct anatomical movements of the limb, and which allows for positioning of the sensors and mechanisms of the brace accordingly to prevent shearing. There is a need for an orthopedic brace that dictates radial and ulnar movement of an arm via a joint positioned closer to the elbow as opposed to the forearm or wrist, where the elbow is the biological director of those movements. In particular, an orthopedic brace with a multiaxial joint that is light, compact, and relatively flat, as to hug the elbow of the user of the orthopedic brace, is needed.

SUMMARY

In concordance with the instant disclosure, an orthopedic brace for a limb, such as for an arm, that better replicates the correct anatomical movements of the limb, and which allows for positioning of the sensors and mechanisms of the brace accordingly to prevent shearing, and which dictates radial and ulnar movement of an arm via a joint positioned closer to the elbow as opposed to the forearm or wrist, where the elbow is the biological director of those movements, and which has a multiaxial joint that is light, compact, and relatively flat, as to hug the elbow of the user of the orthopedic brace, has surprisingly been discovered. The present technology includes articles of manufacture, systems, and processes that relate to an orthopedic method and system.

The present disclosure provides an orthopedic brace for a limb. The orthopedic brace can include an upper portion, a lower portion, and a multi-axial joint. The multi-axial joint can connect the upper portion and the lower portion and can further a stacked joint assembly configured to rotate about multiple axes.

A method of operating an orthopedic system is also provided which includes providing the orthopedic brace and positioning the limb of a user in the orthopedic brace. The method can include supporting movement of the limb, by the user, between a supination position and a pronation position, whereby the limb is supported by the orthopedic brace as well as supporting movement of the limb, by the user, between a flexion position and an extension position, whereby the limb is supported by the orthopedic brace.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Figure 5:
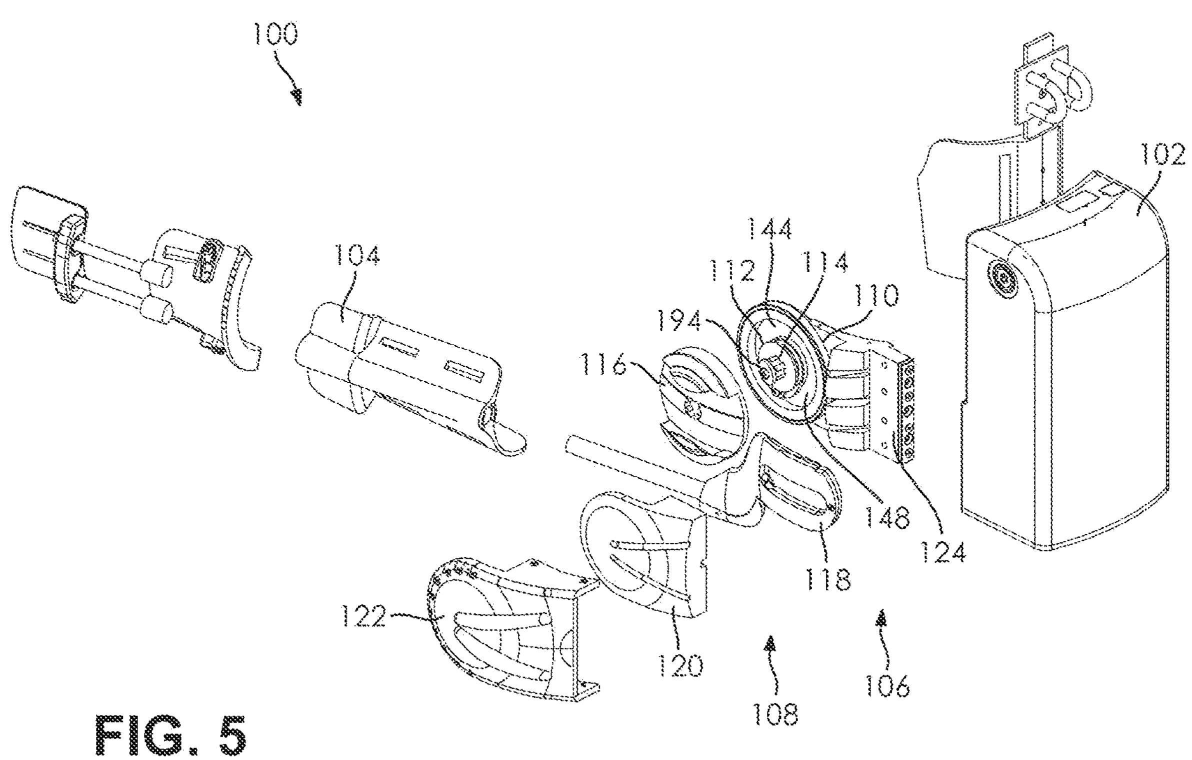
FIG. 5 is an exploded top perspective view of thereof.
Figure 6:
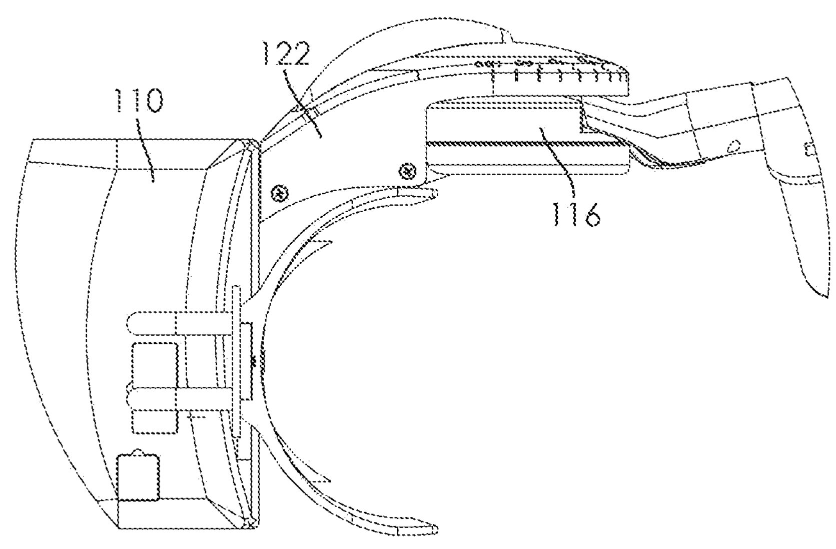
Figure 7:
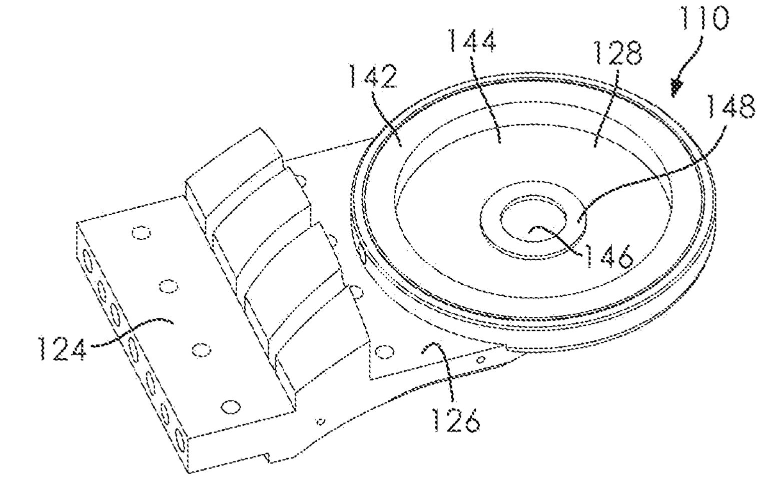
Figure 8:
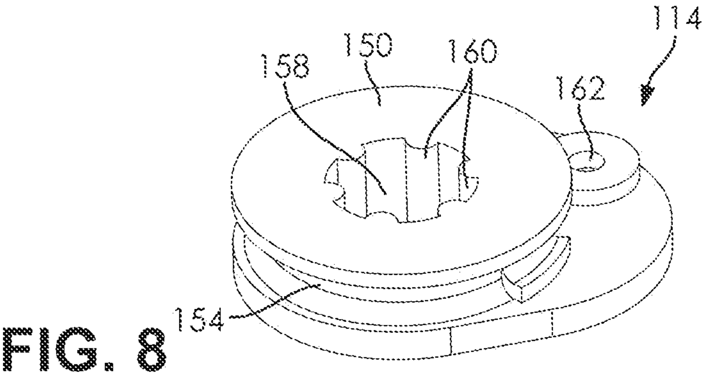
Figure 9:
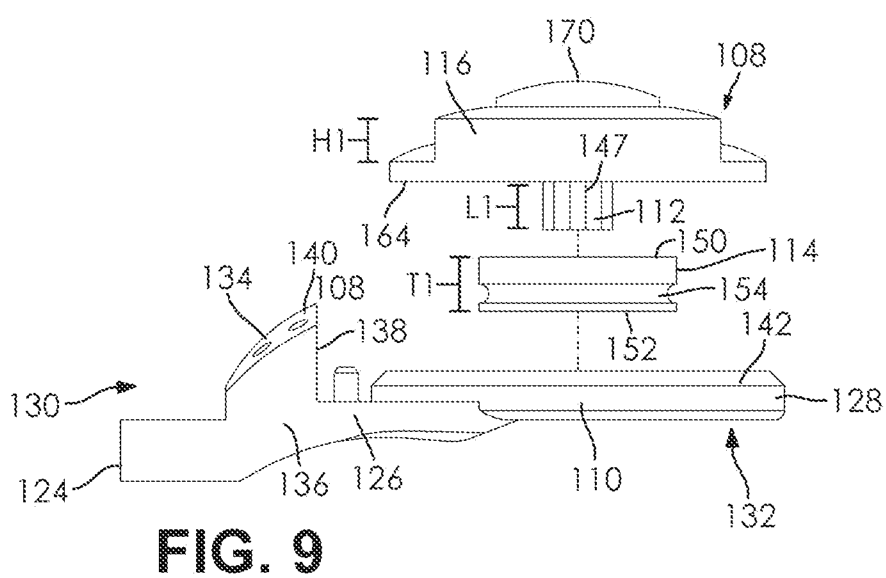
Figure 10:
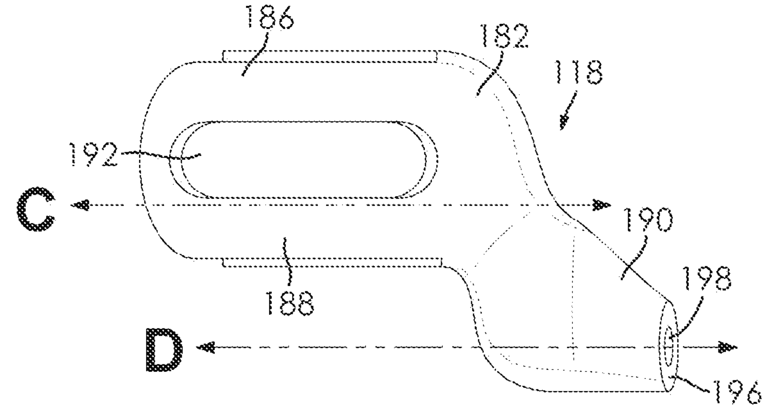
Figure 11:
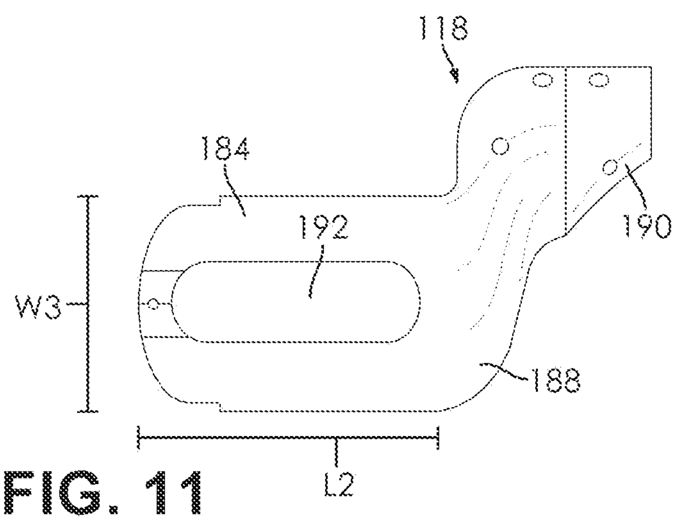
Figure 12:
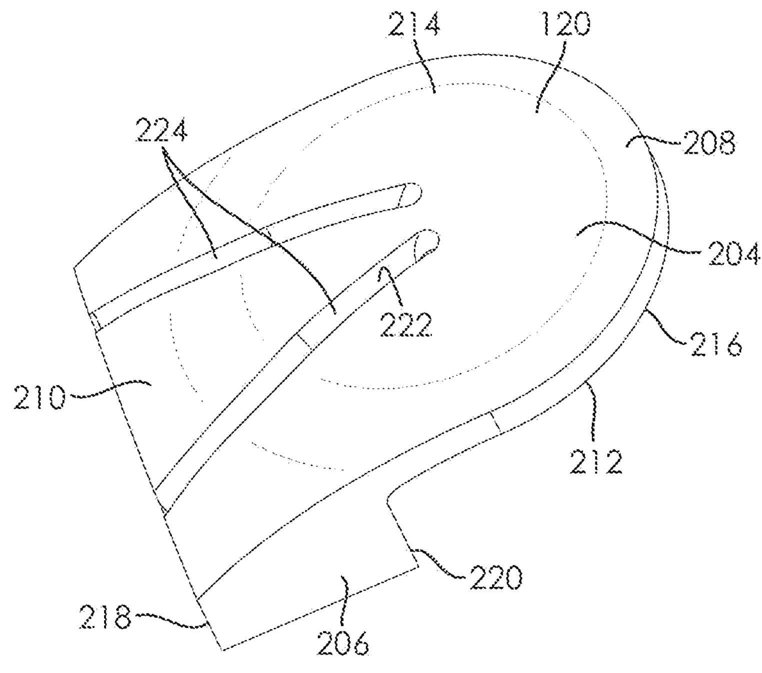
Figure 13:
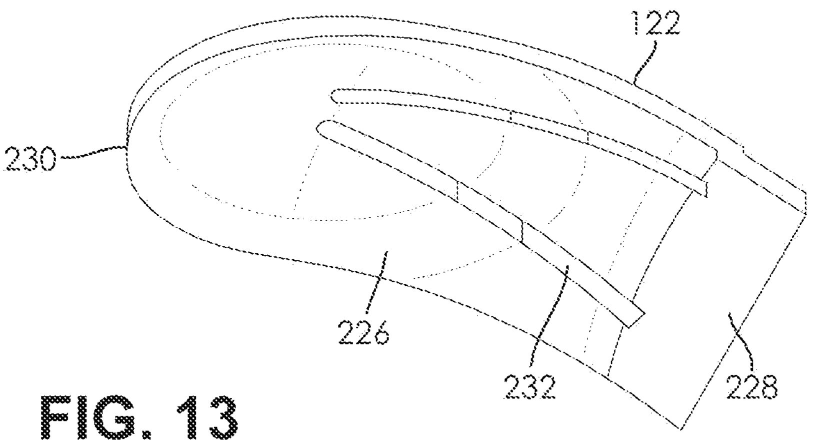
Figure 14A:
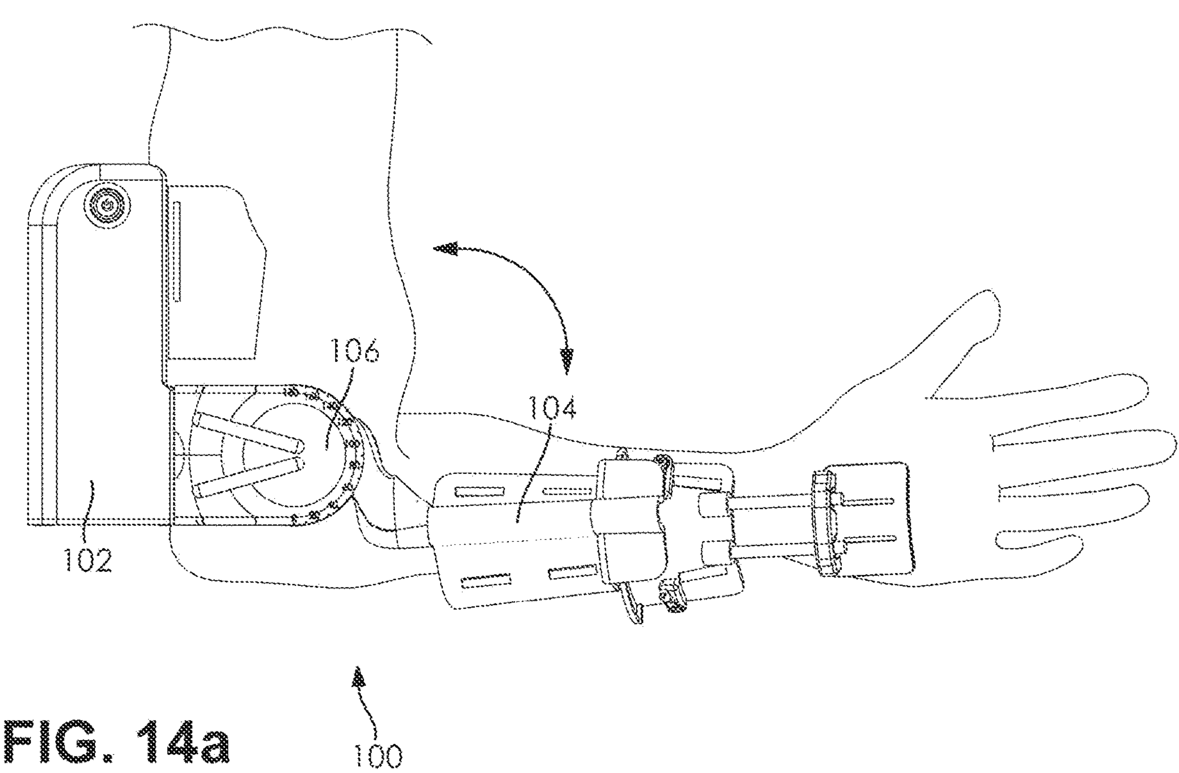
Figure 14B:
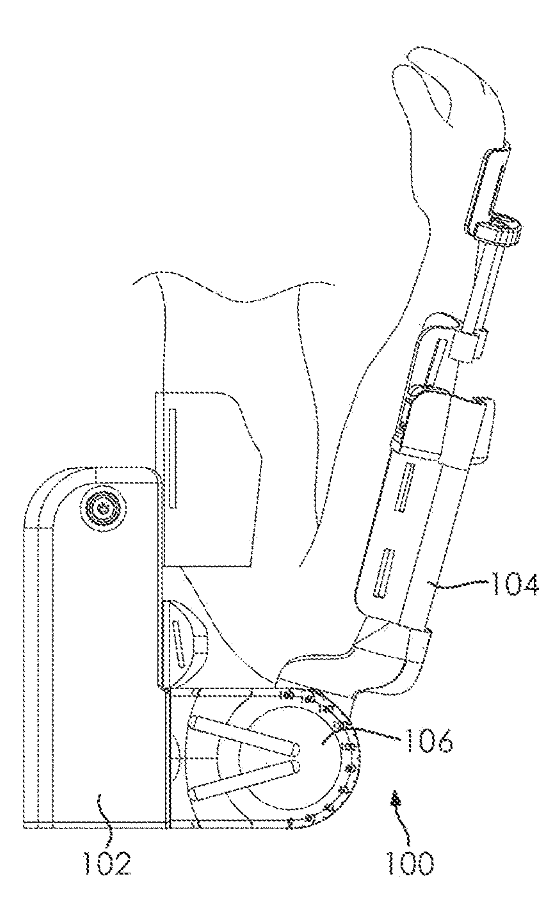
Figure 15A:
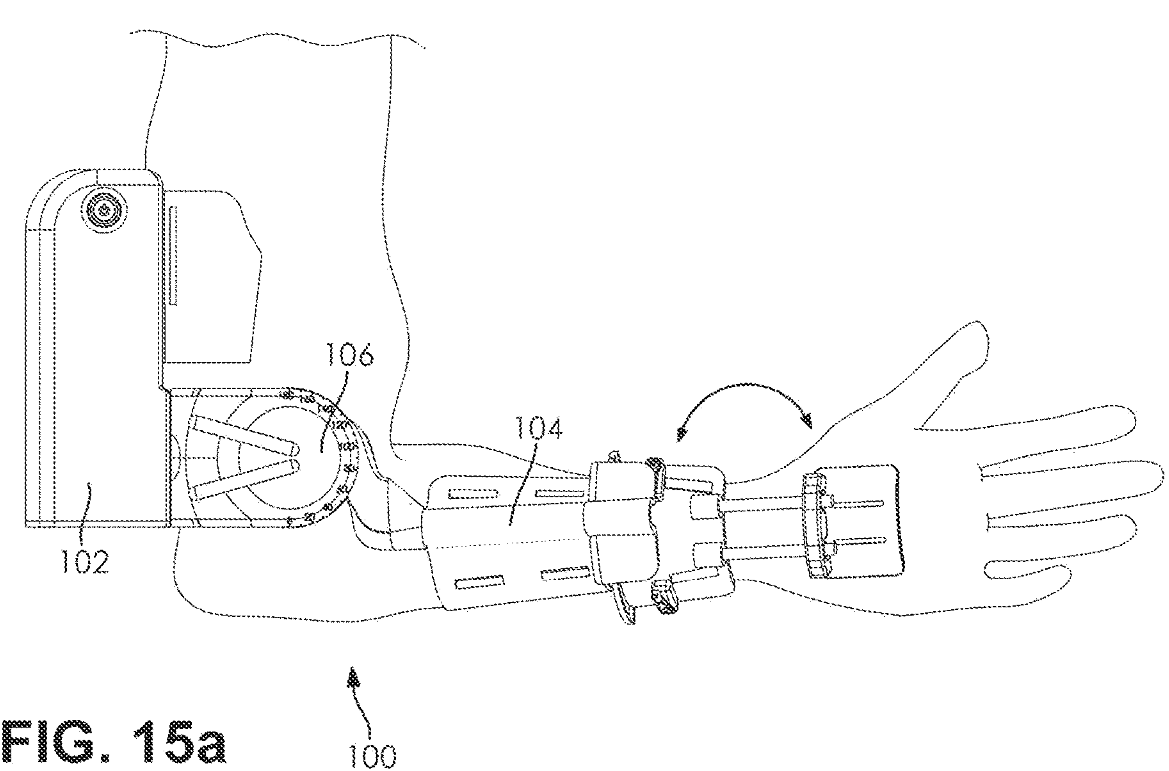
Figure 15B:
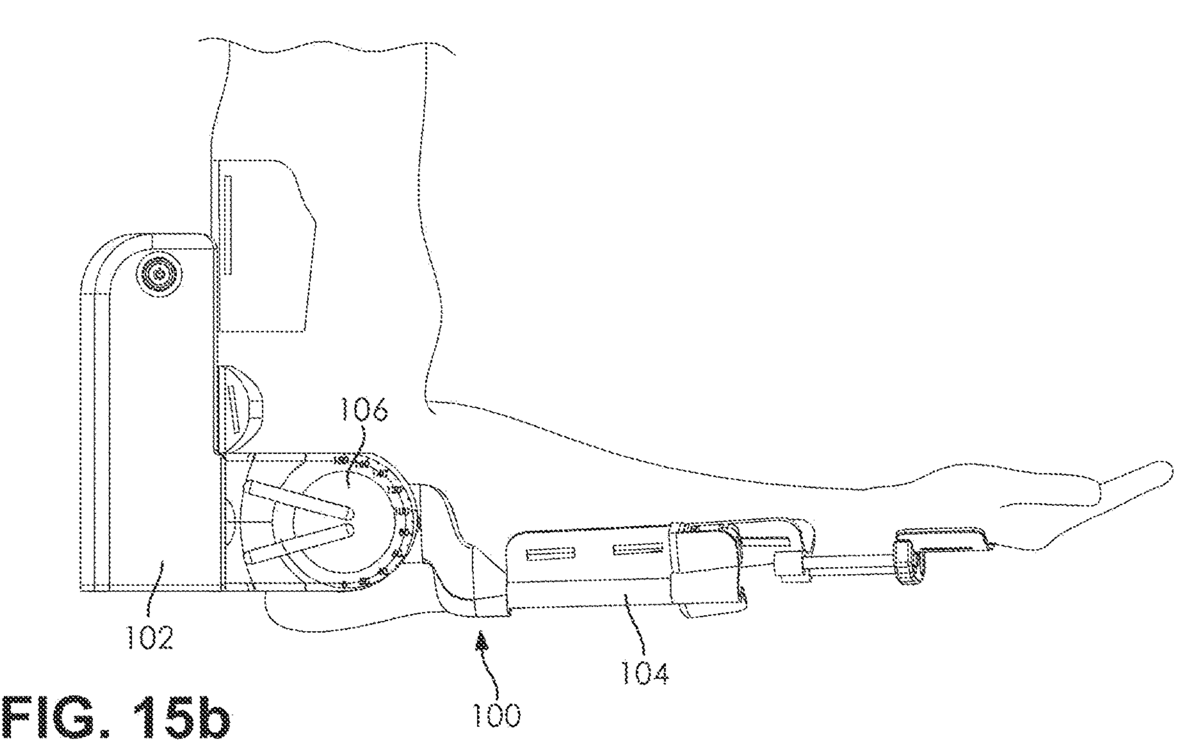
Figure 16:
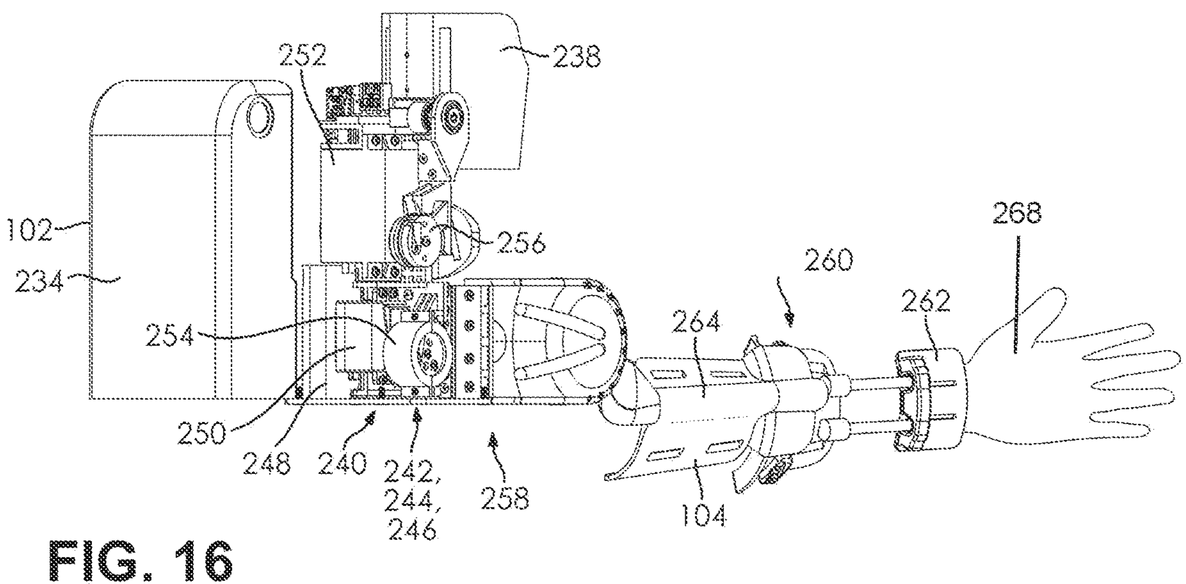
Figure 17:
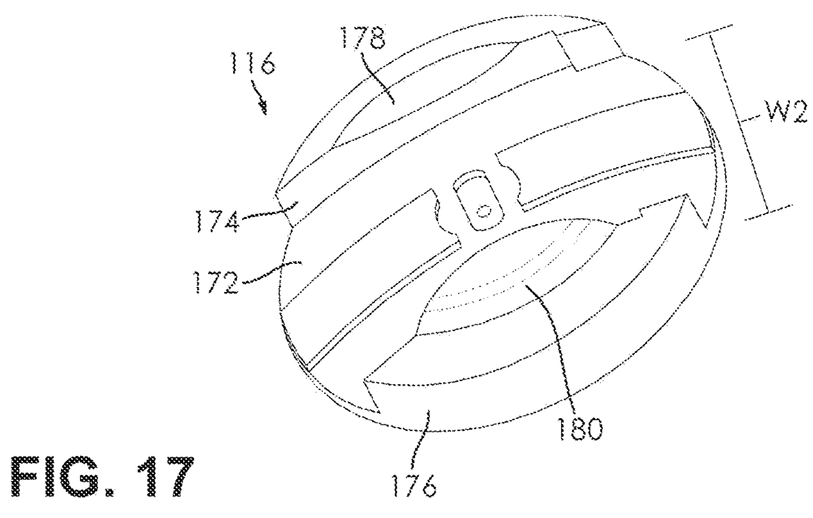
Figure 18:
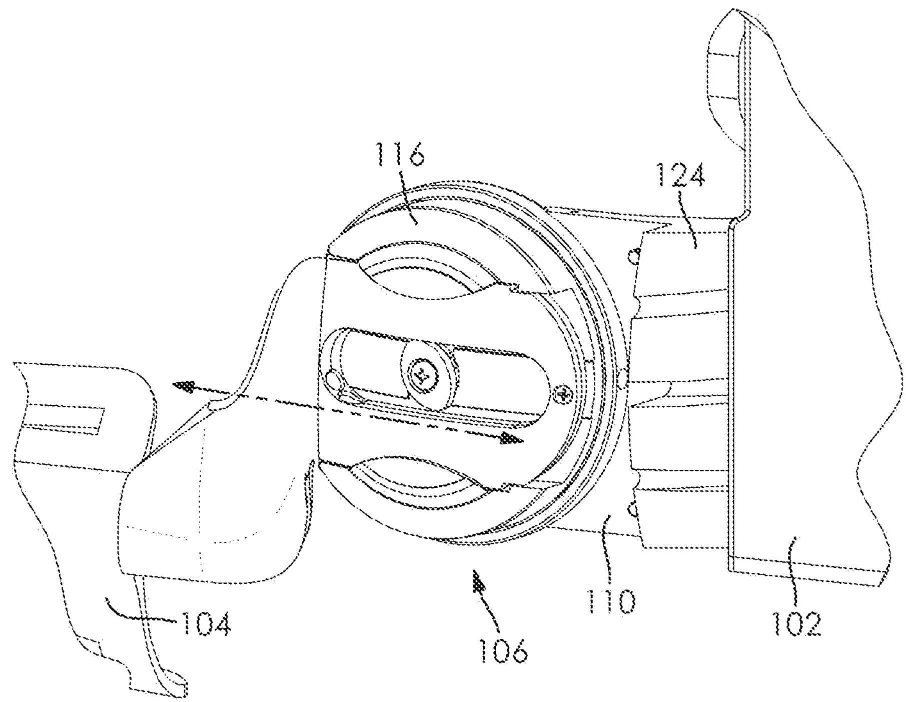
Figure 19:
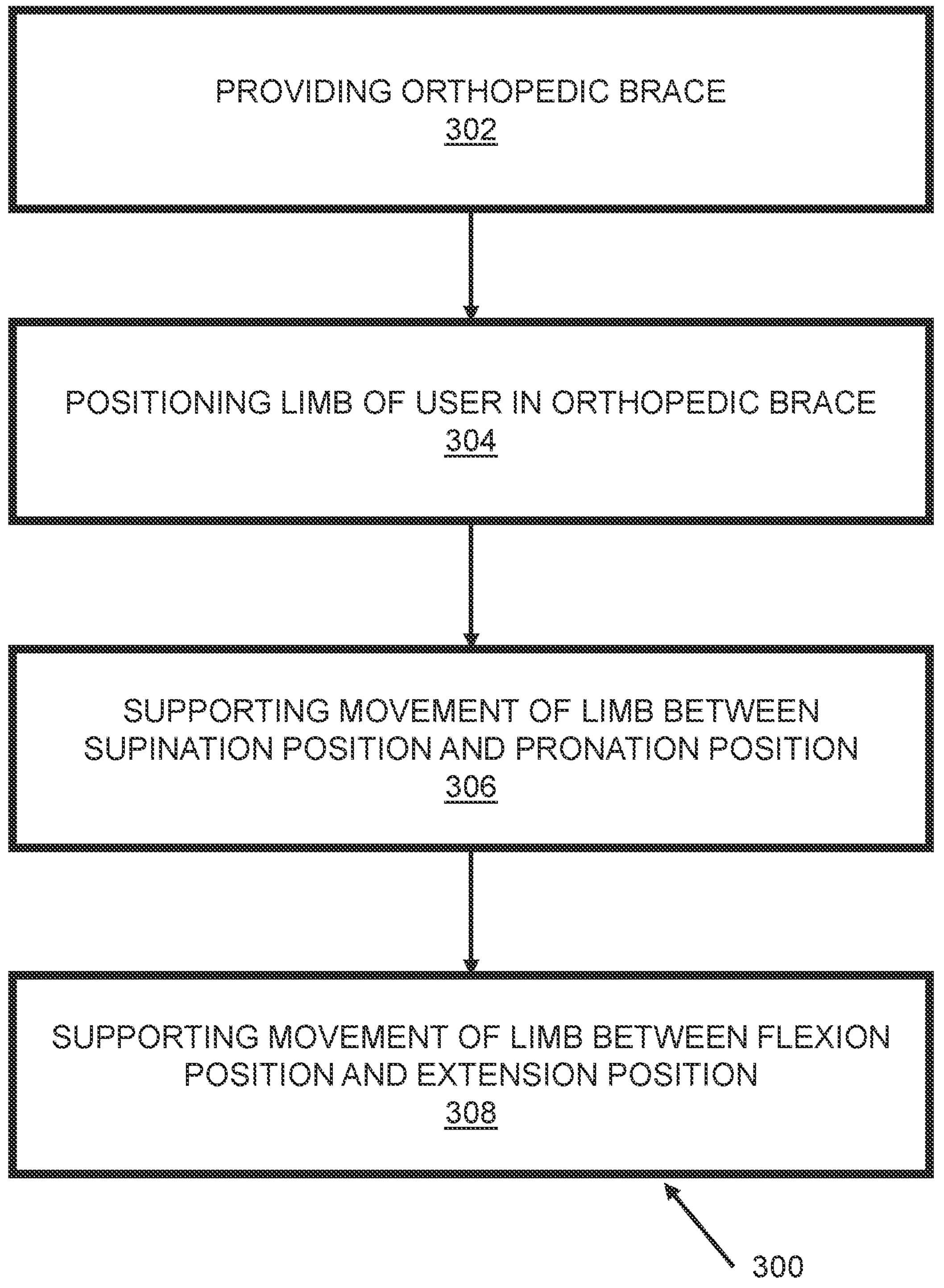

FIG. 5.1 is an exploded view of a pathway for a first disc cable of the multi-axial joint;

FIG. 5.2 is a an exploded view of a pathway for a second disc cable of the multi-axial joint;

FIG. 6 is a top plan view of the multi-axial joint including a stacked joint assembly;

FIG. 7 is a top perspective view of a base of the stacked joint assembly;

FIG. 8 is a top perspective view of a pully disc of the stacked joint assembly;

FIG. 9 is an exploded view of the base, the pulley disc, and a slider housing of the stacked joint assembly;

FIG. 10 is a front elevational view of the slider of the stacked joint assembly, including Axis C and Axis D;

FIG. 11 is a rear elevational view of the slider;

FIG. 12 is a top perspective view of a slider cap of the stacked joint assembly;

FIG. 13 is a bottom perspective view of a cover of the stacked joint assembly;

FIG. 14*a* is an environmental view of the orthopedic brace in operation on a user;

FIG. 14*b* is an environmental view of the orthopedic brace in a flexion position;

FIG. 15*a* is an environmental view of the orthopedic brace in operation on a user;

FIG. 15*b* is an environmental view of the orthopedic brace in a supination position;

FIG. 16 is an exploded view of the upper portion of the orthopedic brace;

FIG. 17 is a top perspective view of the slider housing of the stacked joint assembly;

FIG. 18 is top perspective view of the slider moving within the slider housing; and FIG. 19 is a flow diagram of a method of operating an orthopedic system.

DETAILED DESCRIPTION

The following description of technology is merely exemplary in nature of the subject matter, manufacture and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that can be recited in the art, even though element D is not explicitly described as being excluded herein.

Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter can define endpoints for a range of values that can be claimed for the parameter. For example, if Parameter X is exemplified herein to have value A and also exemplified to have value Z, it is envisioned that Parameter X can have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X can have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it can be directly on, engaged, connected or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

The present technology provides an orthopedic system and method of controlling the same, which can be used in conjunction with the orthopedic system and operation thereof described in co-owned International Patent Application Publication No. WO2022076039 to Seth et al., the entire disclosure of which is incorporated herein by reference. The orthopedic system and method are shown generally in FIGS. 1-19 as an orthopedic brace 100 and a method 300 for operating an orthopedic system. Advantageously, the orthopedic brace 100 of the present disclosure replicates the anatomical movements of a limb by dictating the radial and ulnar movement of the arm. This is achieved by positioning a mechanical joint closer to the elbow as opposed to the forearm or wrist, as the elbow is the biological director of those movements. In this way, the orthopedic brace 100 militates against shearing of the muscle such that layers of tissues slide laterally.

As shown in FIGS. 1-5, the orthopedic brace 100 can include an upper portion 102, a lower portion 104, and a multi-axial joint 106. The multi-axial joint 106 can connect the upper portion 102 and the lower portion 104. The multi-axial joint 106 be mechanical in nature and can include a stacked joint assembly 108 configured to rotate about multiple axes. The stacked joint assembly 108 can include a base 110, a shaft 112, a pulley disc 114, a slider housing 116, a slider 118, a slider cap 120, and a cover 122. It should be appreciated that the stacked joint assembly 108 can operate without being powered by a separate device such as an external battery or power supply source. Advantageously, the stacked joint assembly 108 can provide a robust joint while remaining compact and lightweight.

With reference now to FIGS. 6-9, the base 110 can include a connector 124, a base neck 126, and a foundation 128. The connector 124 of the base 110 can connect the stacked joint assembly 108 to the upper portion 102 of the orthopedic brace 100. With particular reference to FIGS. 7 and 9, the base neck 126 can also include a connector end 130 and a foundation end 132 disposed opposite the connector end 130. The connector end 130 can be attached to the connector 124, and a foundation end 132 that is disposed opposite the connector end 130, which can be attached to the foundation 128. The base neck 126 can also include a protrusion 134 arranged in between the connector end 130 and the foundation end 132. The protrusion 134 can have a connector side 136 facing the connector 124, a foundation side 138 facing the foundation 128, and a top side 140 that is disposed between the connector side 136 and the foundation side 138. The connector side 136 can abut the upper portion 102 of the orthopedic brace 100 and operate in coupling the connector 124 to the upper portion 102. Additionally, the foundation side 138 can abut the slider cap 120 of the stacked joint assembly 108, and the top side 140 can abut the cover 122 of the stacked joint assembly 108. The foundation end 132 of the base 110 can also receive the slider cap 120 of the stacked joint assembly 108. The foundation 128 can also include an outer rim 142 surrounding a recessed lower surface 144. In certain embodiments, aperture 146 can be formed in the recessed lower surface 144 and an inner rim 148 can circumscribe the aperture 146.

Advantageously, the base 110 can act as a support system for the stacked joint assembly 108 and can couple the stacked joint assembly 108 to the upper portion 102. Further, and as described herein, the slider 118 can couple stacked joint assembly 108 to the lower portion 104 of the orthopedic brace 100. In this way, the upper portion 102, the lower portion 104, and the multi-axial joint 106 can work together to provide greater range of motion while the orthopedic brace 100 is in use while still providing support to the user. This is achieved by positioning the multi-axial joint 106 closer to the elbow of the user, as opposed to the forearm or wrist, as the elbow is the biological director of those movements.

With reference to FIG. 9, the shaft 112 of the stacked joint assembly 108 can be rotatably disposed through the aperture 146 of the foundation 128. The shaft 112 can have a shaft length (L1), and the aperture 146 can include an aperture depth (not shown). The shaft length (L1) can be greater than the aperture depth. Further, the shaft 112 can include a plurality of splines 147. Further, the shaft length (L1) can be greater than a total length defined by a sum of the aperture depth of the base and a disc thickness (T1) of the pulley disc 114. It should be appreciated that the shaft 112 can be configured to rotate the slider housing 116 when the pulley disc 114 is rotated, while at the same time, the shaft 112 rotates freely within the aperture 146 in the base. Advantageously, this can provide a greater range of motion for the orthopedic brace 100 by allowing the user to rotate their arm in a natural way, as though they were not wearing the orthopedic brace 100 while still providing support.

With further reference to FIGS. 8-9, the pulley disc 114 can be disposed between the base 110 and the slider housing 116 of the stacked joint assembly 108. The pulley disc 114 can include a first side 150, a second side 152, and the disc thickness (T1) that is defined by a distance between the first side 150 and the second side 152 and shown in FIG. 9. The pulley disc 114 can also include a perimeter channel 154 disposed between the first side 150 and the second side 152. The perimeter channel 154 can be configured to receive a first disc cable 156*a* from the upper portion 102 of the orthopedic brace 100, as shown in FIG. 5.1. The pulley disc 114 can include a grooved aperture 158 that corresponds with the base aperture and that receives the shaft 112 of the stacked joint assembly 108. The grooved aperture 158 can also include a plurality of grooves 160 that align with plurality of splines 147 of the shaft 112. Thus, the shaft 112 can be restricted from rotating within the grooved aperture 158. The pulley disc 114 can also include a cable hole 162 disposed through the pulley disc 114 from the first side 150 to the second side 152, and the cable hole 162 can be configured to secure the first disc cable 156*a* to the pulley disc 114. The pulley disc 114 can act as an intermediary within the stacked joint assembly 108 for the pulley system that runs within the entirety of the orthopedic brace 100, as described herein. In this way, the pulley disc 114 allows for fluid motion and movement of the orthopedic brace 100 while in operation by the user by rotating with the movement of the user.

As shown in FIG. 5, the slider housing 116 can be disposed between the pulley disc 114 and the slider cap 120. Moving now to FIG. 9, the slider housing 116 can include a bottom surface 164. The shaft 112 of the stacked joint assembly 108 can be affixed to the bottom surface 164 of the slider housing 116. The shaft 112 can then be disposed through the pulley disc 114 and inserted into the foundation 128 of the base 110.

With reference to FIGS. 9-11 and 16, the slider housing 116 can include a top surface 170 with an elongated recess 172 that can receive the slider 118 of the stacked joint assembly 108. The elongated recess 172 can include a first side 174 and a second side 176 and each the first side 174 and the second side 176 can include a side height (H1). The first side 174 can have a first lip 178, and the second side 176 can have a second lip 180. Each of the first lip 178 and the second lip 180 can overhang the elongated recess 172. The elongated recess 172 can have an elongated recess width (W2), and the slider 118 can have a slider width (W3). The slider width (W3) can be less than the elongated recess width (W2), such that the slider 118 can be slidably disposed within the elongated recess 172. It should be appreciated that the elongated recess 172 of the slider housing 116 can act as a guide for a second disc cable 156*b*, shown in FIG. 5.2.

As shown in FIG. 5, the slider 118 can be disposed between the slider housing 116 and the slider cap 120. Turning now to FIGS. 10-11, the slider 118 can also include a slider body 182 with a bottom surface 184, a top surface 186, a slider portion 188, and an arm portion 190. A slider opening 192 can be formed in the slider portion 188 of the slider body 182. The slider body 182 can be slidably disposed within the elongated recess 172 of the slider housing 116. Further, the slider portion 188 of the slider body 182 can abut each of the first side 174 and the second side 176 of the elongated recess 172 of the slider housing 116. The top surface 186 of the slider body 182 can abut the first lip 178 and the second lip 180 of the slider housing 116. The slider body 182 can be configured to slide in a lateral movement within the elongated recess 172 of the slider housing 116 further facilitating the movement of the orthopedic brace 100 by the user, as shown in FIG. 18.

With reference to FIGS. 10-11, the slider opening 192 can include a slider opening length (L2). Further, the slider opening 192 can receive a slider stopper 194 that is disposed within the elongated recess 172 of the slider housing 116. The slider stopper 194 can be configured to limit lateral movement of the slider 118. The slider portion 188 of the slider 118 can be oriented on a third axis (C), and the arm portion 190 can be oriented on a fourth axis (D), as shown in FIG. 10. The third axis (C) can be substantially parallel with and offset from the fourth axis (D). Embodiments can include also an arm portion 190 with a terminal end 196 that further has a rod receiver 198. In some embodiments, a rod 202 can be disposed through the lower portion 104 and inserted into the rod receiver 198 of the terminal end 195 of the arm portion 190. In operation, the slider 118 can allow for medial and lateral movement for varus and valgus motions.

With reference to FIG. 5, the slider cap 120 can be disposed between the slider 118 and the cover 122. Turning now to FIG. 12, the slider cap 120 can include a cap body 204 and a cap neck 206. Further, the cap body 204 can include a cap rear end 208, a cap front end 210, a cap bottom side 212, and a cap top side 214. The cap neck 206 can be disposed adjacent the cap rear end 208 and the cap neck 206 can also extend downwardly from the cap body 204. The cap neck 206 can include a cap neck bottom 216, a cap neck rear 218, and a cap neck front 220. With reference to FIGS. 5, 9, and 12, the cap neck bottom 216 of the slider cap 120 can be disposed adjacent the foundation end 132 of the base 110 and the cap neck rear 218 can be disposed adjacent the foundation side 138 of the protrusion 134 of the base 110. The cap neck front 220 can be disposed adjacent to the foundation 128 of the base 110 and also to the slider housing 116. The cap bottom side 212 can be disposed adjacent to each the first lip 178 and a second lip 180 of the slider housing 116. Further, the cap body 204 can also include at least one cable perforation 222 disposed through the cap body 204 from the cap top side 214 to the cap bottom side 212. The at least one cable perforation 222 can be configured to secure the second disc cable 156*b* to the slider cap 120. Further, the cap top side 214 can have at least one cap channel 224 extending between the cap rear end 208 and the cap front end 210, that is configured to receive the second disc cable 156*b*.

As shown in FIG. 13, the cover 122 can include a cover bottom side 226, a cover rear end 228, and a cover front end 230. The cover 122 can be disposed adjacent the cap top side 214 of the slider cap 120. The cover rear end 228 can abut the upper portion 102 of the orthopedic brace 100. The cover bottom side 226 can also include at least one cover cable channel 232, that extends between the cover rear end 228 and the cover front end 230. The at least one cover cable channel 232 can be configured to receive the second disc cable 156*b*.

It should be appreciated that the slider cap 120 and the cover 122 can coordinate with the base 110 to enclose the stacked joint assembly 108. In this way, the internal components of the stacked joint assembly 108, such as the shaft 112, the pulley disc 114, the slider housing 116, and the slider 118, are encased and closed off during use. This can prolong the lifespan of the orthopedic brace 100 by protecting the internal components and militate against dust and debris from entering the stacked joint assembly 108. A skilled artisan can select other suitable housing configurations for the internal components of the stacked joint assembly 108 as desired.

Figure 1:
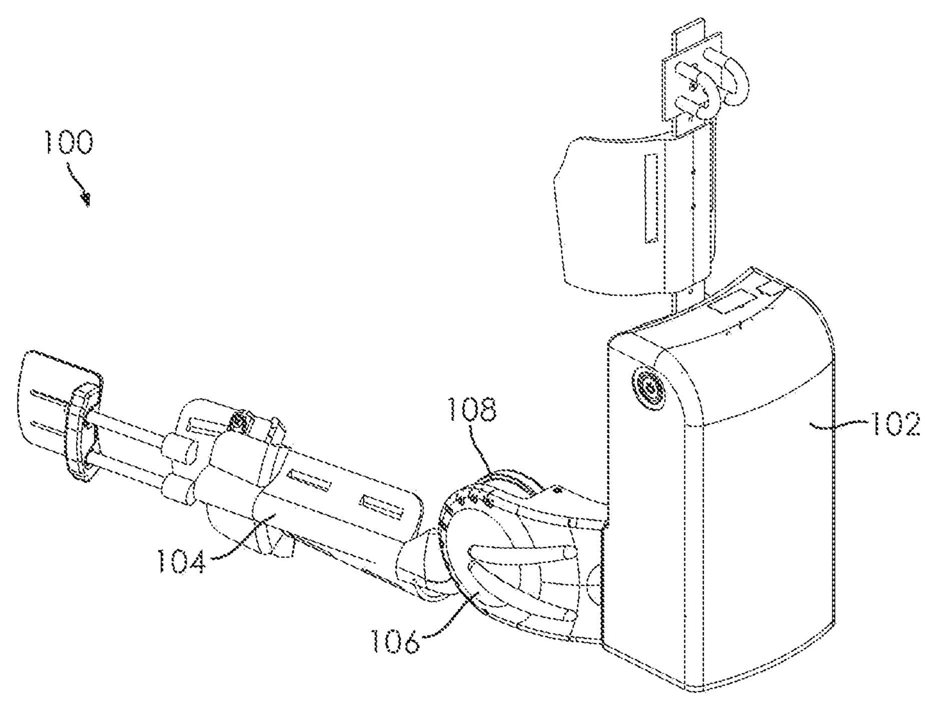
FIG. 1 is a top perspective view of an orthopedic brace including an upper portion, a lower portion, and a multi-axial joint.
Figure 2:
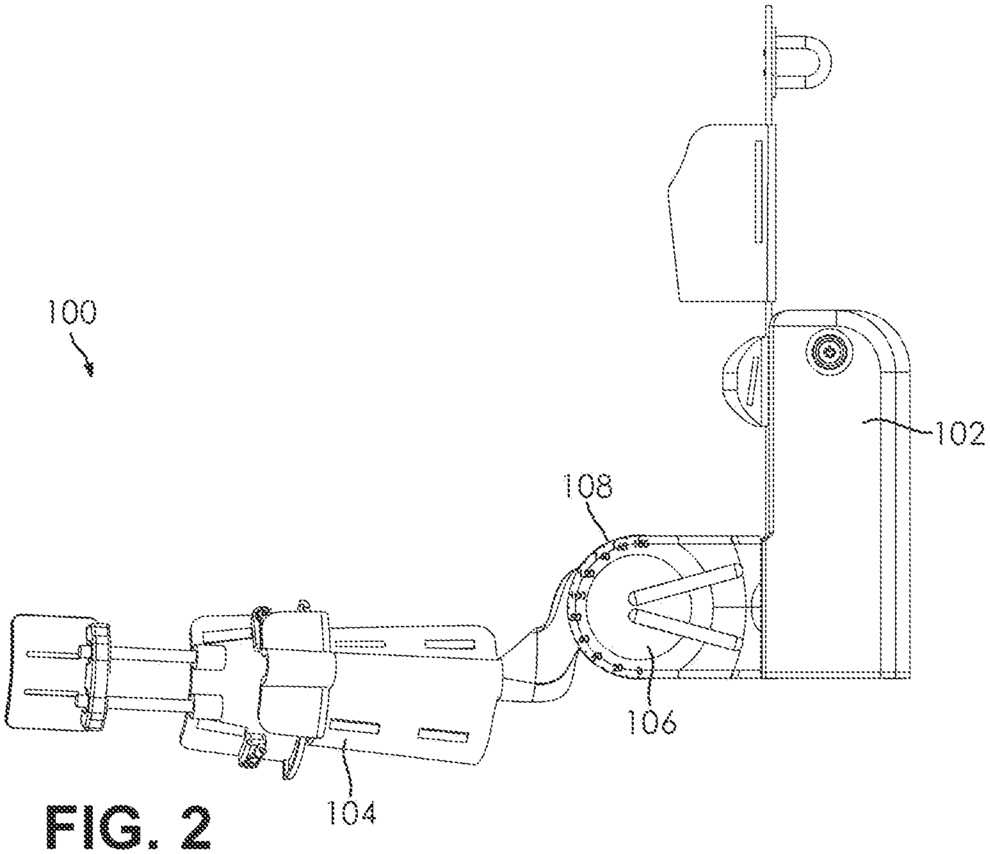
FIG. 2 is a front elevational view thereof.

With reference to FIG. 16, the upper portion 102 of the orthopedic brace 100 can include a housing 234. The upper portion 102 can also include a humeral bar 236 connected to the housing 234 and a humeral cuff 238, as shown in FIG. 1. The humeral cuff 238 can be removable and laterally adjustable along the humeral bar 236. The housing 234 can include a pulley system 240, an actuation assembly 242, a control unit 244, a printed circuit board 246, and at least one removable battery 248. The actuation assembly 242 can cooperate with the control unit 244 where the orthopedic brace 100 is in use. The pulley system 240 can be in communication with the control unit 244 to operate the pulley system 240 where the control unit 244.

With reference to FIG. 16, the pulley system 240 can include a flexion extension servomotor 250, a supination pronation servomotor 252, a flexion-extension pulley 254, a supination-pronation pulley 256, and a cable system 258. It should be appreciated that the pulley system can include more than one cable system in alternative embodiments. Each of the first disc cable 156*a* and the second disc cable 156*b* can be a closed and continuous loop, as shown with reference to the second disc cable 156*b* in FIG. 5.2. Alternatively, each of the first disc cable 156*a* and the second disc cable 156*b* can be an open loop, as shown with reference to the first disc cable 156*b* in FIG. 5.1. A skilled artisan can select a suitable number of cable systems. The cable system 258 can include the first disc cable 156*a* and the second disc cable 156*b* that cooperate to connect the upper portion 102 to the stacked joint assembly 108 and to the lower portion 104. It should be noted that the cable system 258 can include more than one disc cable 156*a*, 156*b* or a single disc cable 156, as an alternative. A skilled artisan can select a suitable number of disc cables 156. The cable system 258 can be configured to connect the pulley system 240 to the pulley disc 114 of the stacked joint assembly 108. The pulley system 240 can then be configured to move the lower portion 104 about the stacked joint assembly 108 between a plurality of positions, including a flexed position, an extended position, a supinated position, and a pronated position. A skilled artisan can select a suitable position within the scope of the present disclosure.

It should further be appreciated that the flexion-extension pulley 254 can work with the second disc cable 156*b*, as shown in FIG. 5.2, to support the joint as it moves between a flexion position and an extension position, as shown in FIGS. 15*a* (neutral) and 15*b* (supination). Similarly, the supination-pronation pulley 256 can work with the first disc cable 156*a*, as shown in FIG. 5.1, to support the joint as it rotates between a supination position and a pronation position, as shown in FIGS. 14*a* (neutral) and 14*b* (flexion). In operation and while used in combination, the flexion-extension pulley 254 and the second disc cable 156*b*, as well as the supination-pronation pulley 256 and the first disc cable 156*a*, provide multiaxial support to the joint.

With continued reference to FIG. 16, the lower portion 104 can include a proximal cuff 260 and a distal cuff 262. The proximal cuff 260 can be disposed between the stacked joint assembly 108 and the distal cuff 262. The proximal cuff 260 can be connected to the slider 118 of the stacked joint assembly 108 with the rod 202. The proximal cuff 260 can be configured to accept a forearm of a user, and the distal cuff 262 can be configured to accept a wrist and a hand of the user, as shown in FIG. 14. In a most particular embodiment, the distal cuff 262 can include a forearm section configured to accept the forearm of the user, and a wrist-hand section configured to accept the wrist and the hand of the user.

Figure 3:
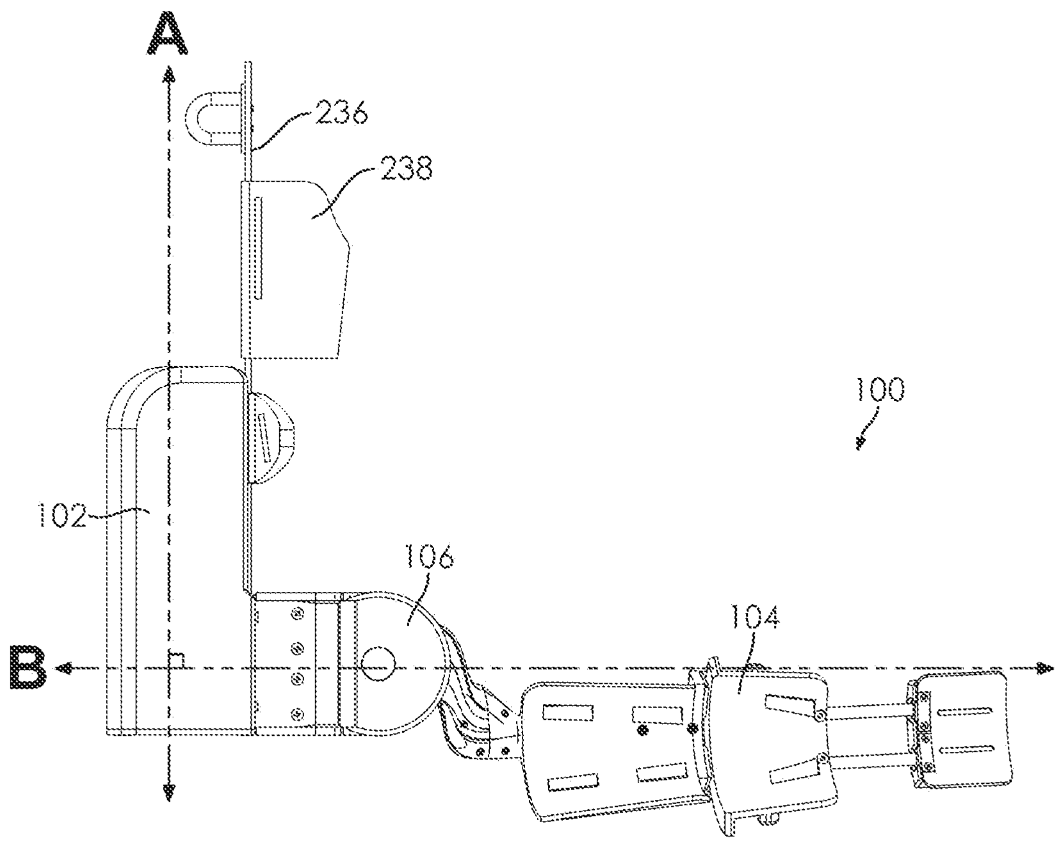
FIG. 3 is a rear elevational view of the orthopedic brace, including Axis A and Axis B, disposed orthogonally.
Figure 4:
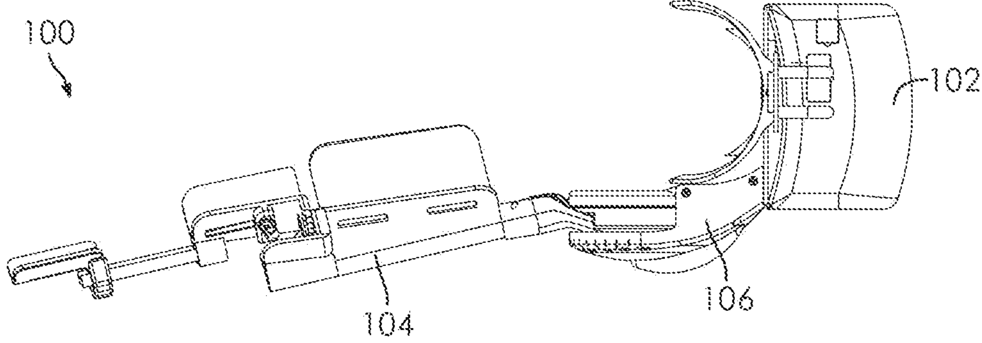
FIG. 4 is a top plan view of the orthopedic brace.

Other aspects of the orthopedic brace 100 can include the following. The rod 202 can also be configured to receive the disc cable 156. The proximal cuff 260 can be connected to the distal cuff 262 with at least one cuff rod configured to receive the disc cable 156. The upper portion 102 can be aligned with a first axis (A) while the base 110 of the stacked joint assembly 108 can be aligned with a second axis (B), as shown in FIG. 3. The second axis (B) can be oriented substantially orthogonal with the first axis (A). In a most particular embodiment, the second axis can be orientated at about a 90-degree angle relative to the first axis. In an alternative embodiment of the orthopedic brace 100, the shaft 112 of the stacked joint assembly 108 is not connected to the slider housing 116. Further, the slider 118 can include the slider opening 192 that has plurality of opening grooves 266. The opening grooves 266 can align with the plurality of splines 147 on the shaft 112 of the stacked joint assembly 108, which allow the slider 118 to move laterally. Lateral movement of the slider 118 can then be limited by the shaft 112 which is disposed within the slider opening 192 of the slider 118.

The present disclosure further provides a method 300 of operating an orthopedic system, as shown in FIG. 19. The method 300 can include a step 302 of providing an orthopedic brace 100 for an arm. In certain embodiments the orthopedic brace 100 can include the orthopedic brace of the present disclosure, as described above, which includes an upper portion 102, a lower portion 104, and a multi-axial joint 106 connecting the upper portion 102 and the lower portion 104. The multi-axial joint 106 can include a stacked joint assembly 108 configured to rotate about multiple axes and described herein.

The method 300 can include a step 304 of positioning the limb of a user in the orthopedic brace 100. It should be appreciated that the orthopedic brace 100 can include an over the shoulder strapping or an attachment style loop for securing the orthopedic brace 100 to the user. The orthopedic brace 100 can further include a glove 268 disposed adjacent to the distal cuff 262, as shown in FIG. 16, for securing the orthopedic brace 100 to the user. A skilled artisan can select a suitable securing mechanism for the orthopedic brace 100 within the present disclosure.

The method 300 can include a step 306 of supporting movement of the limb, by the user, between a supination position and a pronation position, whereby the limb is supported by the orthopedic brace 100. The method 300 can further include a step 308 of supporting movement of the limb, by the user, between a flexion position and an extension position, whereby the limb is supported by the orthopedic brace 100.

As described herein, the orthopedic brace 100 replicates the anatomical movements of the limbs by dictating the radial and ulnar movement of the arm. This is achieved by positioning the multi-axial joint 106 closer to the elbow, as opposed to the forearm or wrist, as the elbow is the biological director of those movements. In this way, the orthopedic brace 100 militates against shearing.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments can be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. An orthopedic brace for a limb, comprising:
an upper portion;
a lower portion including a proximal cuff and a distal cuff; and
a multi-axial joint connecting the upper portion and the lower portion, the multi-axial joint having a stacked joint assembly being mechanical and configured to rotate about multiple axes, wherein the proximal cuff is disposed between the stacked joint assembly and the distal cuff, and the proximal cuff is connected to a slider of the stacked joint assembly with a rod, the stacked joint assembly including:
a base coupled to the upper portion;
a shaft rotatably disposed through the base;
a slider housing coupled to the base and disposed adjacent to the shaft, the slider housing including an elongated recess having a longitudinal axis parallel with the rod;
a pulley disc disposed between the base and the slider housing and configured to be slidably disposed on the shaft;
the slider disposed adjacent to and nested within the elongated recess of the slider housing, the slider having a transverse oriented coupling to the rod such that the rod and slider are transversely offset;
a slider cap disposed on to the slider; and
a cover disposed on the slider cap.

2. The orthopedic brace of claim 1, wherein the upper portion includes:
a housing;
a humeral bar connected to the housing; and
a humeral cuff that is removable and laterally adjustable along the humeral bar.

3. The orthopedic brace of claim 2, wherein the housing includes a pulley system, an actuation assembly, a control unit, a printed circuit board, and a removable battery.

4. The orthopedic brace of claim 3, wherein the pulley system includes a flexion extension servo, a supination pronation servo, a flexion-extension pulley, a supination-pronation pulley, and a cable system.

5. The orthopedic brace of claim 4, wherein the cable system includes a first disc cable and a second disc cable for connecting the upper portion to the stacked joint assembly and the lower portion.

6. The orthopedic brace of claim 5, wherein the cable system connects the pulley system to a pulley disc of the stacked joint assembly, and the pulley system is configured to move the lower portion about the stacked joint assembly between a plurality of positions.

7. The orthopedic brace of claim 6, wherein the plurality of positions includes a flexed position, an extended position, a supinated position, and a pronated position.

8. The orthopedic brace of claim 1, wherein the base includes:
a connector configured to couple the stacked joint assembly to the upper portion;
a base neck disposed adjacent to the connector; and
a foundation for receiving the shaft.

9. The orthopedic brace of claim 8, wherein the upper portion of the orthopedic brace has an opening into which the connector of the base is inserted and the connector is affixed to the upper portion and does not move relative to the upper portion.

10. The orthopedic brace of claim 1, wherein the upper portion is aligned with a first axis, the base of the stacked joint assembly is aligned with a second axis, and the second axis is oriented substantially orthogonal with the first axis.

11. The orthopedic brace of claim 1, wherein the pulley disc has a first side, a second side, a perimeter channel disposed between the first side and the second side, and a disc thickness defined by a distance between the first side and the second side.

12. The orthopedic brace of claim 1, wherein the slider housing has a top surface and a bottom surface, the bottom surface concave and disposed adjacent the pulley disc.

13. The orthopedic brace of claim 1, wherein the slider includes a slider body having a bottom surface, a top surface, a slider portion, and an arm portion for coupling with the lower portion.

14. The orthopedic brace of claim 1, wherein the slider cap has a cap body cooperating with the slider and a cap neck coordinating with the base.

15. The orthopedic brace of claim 1, wherein the proximal cuff is configured to accept a forearm of a user.

16. A method of supporting a limb using an orthopedic brace, the method comprising steps of:
providing the orthopedic brace for the limb of claim 1;
positioning the limb of a user in the orthopedic brace;
supporting movement of the limb, by the user, between a supination position and a pronation position, whereby the limb is supported by the orthopedic brace; and
supporting movement of the limb, by the user, between a flexion position and an extension position, whereby the limb is supported by the orthopedic brace.

17. An orthopedic brace for a limb, comprising:
an upper portion including:
an opening,
a housing,
a humeral bar connected to the housing, and
a humeral cuff that is removable and laterally adjustable along the humeral bar;
a lower portion including a proximal cuff and a distal cuff; and
a multi-axial joint connecting the upper portion and the lower portion, the multi-axial joint having a stacked joint assembly being mechanical and configured to rotate about multiple axes, wherein the proximal cuff is disposed between the stacked joint assembly and the distal cuff, and the proximal cuff is connected to a slider of the stacked joint assembly with a rod, the stacked joint assembly including:

a base coupled to the upper portion, the base including:
 a connector configured to couple the stacked joint assembly to the upper portion, the connector configured to be inserted into the opening of the upper portion and affixed to the upper portion,
 a base neck disposed adjacent to the connector, and
 a foundation;
a shaft rotatably disposed through the base;
a slider housing coupled to the base and disposed adjacent to the shaft, the slider housing including a top surface and a bottom surface, the bottom surface being concave, the slider housing including an elongated recess having a longitudinal axis parallel with the rod;
a pulley disc disposed between the base and the slider housing and configured to be slidably disposed on the shaft, the pulley disc including:
 a first side,
 a second side,
 a perimeter channel disposed between the first side and the second side, and
 a disc thickness defined by a distance between the first side and the second side;
the slider disposed adjacent to and nested within the elongated recess of the slider housing, the slider having a transverse oriented coupling to the rod such that the rod and slider are transversely offset, the slider including a slider body having a bottom surface, a top surface, a slider portion, and an arm portion for coupling with the lower portion;
a slider cap disposed on to the slider, the slider cap including a cap body cooperating with the slider and a cap neck coordinating with the base; and
a cover disposed on the slider cap,
wherein the upper portion is aligned with a first axis, the base of the stacked joint assembly is aligned with a second axis, and the second axis is oriented substantially orthogonal with the first axis.

* * * * *